United States Patent [19]

Richard et al.

[11] Patent Number: 5,945,389
[45] Date of Patent: Aug. 31, 1999

[54] PERSONAL CLEANSING SOAP-SYNTHETIC BAR COMPOSITIONS WITH LOW LEVELS OF NONIONIC, POLYETHYLENE/POLYPROPYLENE GLYCOL POLYMERS FOR IMPROVED MILDNESS

[75] Inventors: Marilyn Ann Richard, Cincinnati; Sherri Vesalga Cox; James Charles Dunbar, both of West Chester, all of Ohio

[73] Assignee: The Proctor & Gamble Company, Cincinnati, Ohio

[21] Appl. No.: 08/590,805

[22] Filed: Jan. 24, 1996

Related U.S. Application Data

[63] Continuation of application No. 08/240,190, May 10, 1994, abandoned.

[51] Int. Cl.$^6$ .............................. A61K 7/50; C11D 17/00
[52] U.S. Cl. .................... 510/153; 510/141; 510/155; 510/484; 510/447; 510/450
[58] Field of Search ..................... 510/141, 152, 510/155, 156, 447, 450, 475, 484

[56] References Cited

U.S. PATENT DOCUMENTS

| | | | |
|---|---|---|---|
| 3,248,333 | 4/1966 | O'Roark | 252/144 |
| 3,598,746 | 8/1971 | Kaniecki et al. | 252/122 |
| 3,835,057 | 9/1974 | Cheng et al. | 252/107 |
| 3,864,272 | 2/1975 | Toma et al. | 252/125 |
| 4,169,067 | 9/1979 | Joshi | 252/132 |
| 4,256,600 | 3/1981 | Lewis et al. | 252/132 |
| 4,285,826 | 8/1981 | Bertozzi et al. | 252/117 |
| 4,582,626 | 4/1986 | Ferrara . | |
| 4,673,525 | 6/1987 | Small et al. . | |
| 5,154,849 | 10/1992 | Visschei et al. | 252/174.15 |
| 5,204,014 | 4/1993 | Redd et al. | 252/117 |

FOREIGN PATENT DOCUMENTS

| | | | |
|---|---|---|---|
| 0 251 410 A1 | 1/1988 | European Pat. Off. | C11D 9/26 |
| 0 283 091A1 | 9/1988 | European Pat. Off. | C11D 9/26 |
| 6-3008-498 | 6/1988 | Japan | C11D 1/83 |
| 05098291 | 1/1991 | Japan | C11D 1/83 |
| 05262639 | 3/1992 | Japan | A61K 7/50 |
| 1 566 810 | 5/1980 | United Kingdom | C11D 10/06 |
| 1 573 529 | 8/1980 | United Kingdom | C11D 10/06 |
| WO 92/13060 | 8/1992 | WIPO | C11D 17/00 |
| WO 93/07245 | 4/1993 | WIPO | A61K 7/08 |

OTHER PUBLICATIONS

*J. Invest. Dermatol.*, T. J. Franz, 1975, 64, pp. 190–195.
Amerchol Trade Brochure Re: Polyox, Mar. 1991.

*Primary Examiner*—Margaret Einsmann
*Attorney, Agent, or Firm*—Darryl C. Litttle; Tara M. Rosnell; George W. Allen

[57] ABSTRACT

The present invention relates to personal cleansing bar compositions comprising:

A. from about 1 parts to about 70 parts by bar weight of a mild synthetic surfactant selected from the group consisting of sodium cocoyl isethionate, sodium topped cocoyl isethionate, essentially saturated $C_{15}$–$C_{22}$ alkyl sulfate, essentially saturated $C_{15}$–$C_{22}$ alkyl sarcosinate, essentially saturated $C_{15}$–$C_{22}$ alkyl glyceryl ether sulfonate, and mixtures thereof;

B. from about 0.01 parts to about 1 parts by bar weight of a nonionic polymer;

wherein the nonionic polymer is selected from the group consisting of:

$$H(O[CH_2]_x)_nOH; \tag{I}$$

$$H[OCH_2CH]_nOH; \text{ and} \atop {|} \atop CH_3 \tag{II}$$

mixtures thereof; $\tag{III}$ wherein x is 2; and n has an average value of from about 2,000 to about 115,000 and wherein the pH is from about 4 to about 9. These bar compositions provide enhanced clinical mildness to the skin while maintaining good lathering, increased lather lubricity and lather creaminess.

10 Claims, No Drawings

5,945,389

PERSONAL CLEANSING SOAP-SYNTHETIC BAR COMPOSITIONS WITH LOW LEVELS OF NONIONIC, POLYETHYLENE/ POLYPROPYLENE GLYCOL POLYMERS FOR IMPROVED MILDNESS

This is a continuation of application Ser. No. 08/240,190, filed May 10, 1994 now abandoned.

TECHNICAL FIELD

The present invention relates to personal cleansing soap-synthetic bars containing acyl isethionate and low levels of nonionic polyethylene/polypropylene glycol polymers which provide enhanced clinical mildness to the skin while maintaining good lathering.

BACKGROUND OF THE INVENTION

The present invention relates to sodium acyl isethionate based skin cleansing toilet bars with improved mildness. In other words, this invention relates to skin cleansing toilet bars comprising sodium acyl isethionate as a primary synthetic surfactant.

The cleansing of skin with more mild surface-active cleansing preparations has become a focus of great interest. Many people wash and exfoliate their skin with various surface-active preparations several times a day. Ideal skin cleansers should cleanse the skin gently, causing little or no irritation, without defatting and overdrying the skin or leaving it taut after frequent routine use. Most lathering soaps, liquids and bars included, fail in this respect.

Synthetic detergent bars, frequently referred to as "combo bars" and/or "syndet bars," are known and are becoming increasingly popular due to their increasing mildness. However, widespread replacement of soap bars by syndet bars has not so far been possible for a variety of reasons, primarily the poor physical characteristics of syndet bars as compared to soap bars, e.g., off odors, poor processability, stickiness, brittleness, smear or bar messiness, lather quality or combinations thereof.

Sodium acyl isethionate combo bars are, per se, old in the art, e.g., mild sodium acyl isethionate synthetic surfactant based personal cleansing bars are also disclosed in U.S. Pat. No. 2,894,912, issued July 1959, to Geitz and U.S. Pat. No. 4,954,282, Rys, et al., issued Sep. 4, 1990.

Therefore, the object of the present invention is to provide a syndet bar which has enhanced clinical mildness while providing good lathering, increased lather lubricity and creaminess.

It is a further object of the present invention to provide a syndet bar with enhanced clinical mildness while providing a bar composition which is easily processable.

SUMMARY OF THE INVENTION

The present invention relates to personal cleansing bar compositions comprising:

A. from about 1 parts to about 70 parts by bar weight of a mild synthetic surfactant selected from the group consisting of sodium cocoyl isethionate, sodium topped cocoyl isethionate, essentially saturated $C_{15}$–$C_{22}$ alkyl sulfate, essentially saturated $C_{15}$–$C_{22}$ alkyl sarcosinate, essentially saturated $C_{15}$–$C_{22}$ alkyl glyceryl ether sulfonate, and mixtures thereof;

B. from about 0.01 parts to about 1 parts by bar weight of a nonionic polymer;

C. from about 0 parts to about 50 parts by bar weight of a wax having a melting point of from about 130° F.(54° C.) to about 180° F.(82° C.);

D. from about 0 parts to about 60 parts by bar weight lathering mild synthetic surfactant selected from the group consisting of methyl acyl taurates, N-acyl glutamates, alkyl sulfosuccinates, alkyl phosphate esters, ethoxylated alkyl phosphate esters, trideceth sulfates, ethoxylated alkyl sulfates and alkyl amine oxides, betaines, sultaines, $C_{12}$–$C_{14}$ alkyl glyceryl ether sulfonate, $C_{12}$–$C_{18}$ acyl sarcosinate, and mixtures thereof;

E. from about 0 parts to about 35 parts by bar weight fatty acid;

F. from about 0 parts to about 20 parts by bar weight sodium soap;

G. from about 0 to about 50 parts by bar weight Mg soap;

H. from about 0 parts to about 15 parts by bar weight sodium isethionate;

I. from 0 parts to about 5 parts by bar weight sodium chloride;

J. from about 3 parts to about 30 parts by bar weight water; and wherein the nonionic polymer is selected from the group consisting of:

$$H(O[CH_2]_x)_nOH; \qquad (I)$$

$$H[OCH_2CH]_nOH; \text{ and} \qquad (II)$$
$$\phantom{H[OCH_2CH]_nOH;}\; |$$
$$\phantom{H[OCH_2CH]_nOH;}\; CH_3$$

$$\text{mixtures thereof;} \qquad (III)$$

wherein x is 2; and n has an average value of from about 2,000 to about 115,000 and wherein the pH is from about 4 to about 9. These bar compositions provide enhanced clinical mildness to the skin while maintaining good lathering, increased lather lubricity and lather creaminess.

The percentages, ratios, and parts herein are on a total bar composition weight basis, unless otherwise specified. All levels and ranges herein are approximations, unless otherwise specified.

All measurements are made at 25° C., unless otherwise designated. The invention herein can comprise, consist of, consist essentially of, the essential components as well as the optional components as described herein.

DETAILED DESCRIPTION OF THE INVENTION

The present invention relates to bar compositions comprising from about 10 parts to about 70 parts by bar weight of sodium cocoyl isethionate (SCI).

Preferably the present invention relates to a personal cleansing bar composition comprising from about 10 part to about 70 parts by bar weight of a sodium distilled, topped acyl (preferably $C_{12}$–$C_{18}$ acyl, more preferably topped cocoyl) isethionate or "Sodium Topped Cocoyl Isethionate" (STCI). Bar compositions containing STCI are more easily processable, mild, have reduced odor versus those bars made with ordinary sodium cocoyl isethionate (SCI), etc.

The term "Sodium Topped Cocoyl Isethionate" or "STCI" as used herein means that the cocoyl (acyl) groups have the following carbon chain lengths: from zero to about 4% by weight of the total STCI, of a highly soluble acyl groups such as $C_6$, $C_8$, $C_{10}$, $C_{18:1}$, and $C_{18:2}$; from about 45% to about 65% $C_{12}$, preferably from about 50% to about 60% $C_{12}$; and from about 30% to about 55%, preferably from about 35 to about 50% of $C_{14}$, $C_{16}$ and $C_{18}$.

Preferably any STCI highly soluble acyl groups ($C_6$, $C_8$, etc.) are from zero to below about 3% by weight of the total STCI. More preferably the low melting acyl isethionates are less than 2.8 parts by weight of the bar and are preferably, zero when the total level of STCI is low.

The bars of present invention are more easily processable with higher levels of moisture, without expected processing negatives. Increased bar moisture contributes to better bar lather. Use of the sodium topped cocoyl isethionate also allows for an increase in levels of other hygroscopics, such as alkyl glyceryl sulfonate (AGS) and alkyl ether(3) sulfate ($AE_3S$), in the bar formulation without exhibiting processing negatives that would otherwise be experienced using regular SCI.

More specifically, the SCI and/or STCI bar composition of this invention comprises the following components set out in Table A in parts by weight of the bar.

TABLE A

| Component in Parts | Range | Preferred Range | More Preferred Range |
|---|---|---|---|
| A. SCI/STCI | 10 to 70 | 12 to 60 | 15 to 50 |
| B. Na-Alkyl Glyceryl Ether Sulfonate | 0 to 50 | 5 to 30 | 10 to 20 |
| C. Na-Alkyl Ether Sulfate | 0 to 10 | 1 to 8 | 2 to 6 |
| D. Na-Cetearyl Sulfate | 0 to 40 | 4 to 30 | 8 to 20 |
| E. Na-soap | 0 to 20 | 1 to 15 | 2 to 12 |
| F. Mg-soap | 0 to 50 | 1 to 30 | 3 to 20 |
| G. Fatty Acid | 0 to 35 | 3 to 25 | 5 to 20 |
| H. Paraffin | 0 to 50 | 3 to 45 | 5 to 40 |
| I. NaCl | 0 to 5 | 0.1 to 3 | 0.2 to 2 |
| J. Na2SO4 | 0 to 5 | 0.1 to 3 | 0.2 to 2 |
| K. Na-Isethionate | 0 to 15 | 1 to 10 | 2 to 8 |
| L. Water | 3 to 30 | 4 to 15 | 5 to 10 |
| M. Fragrance | 0 to 2 | 0.5 to 1.5 | 0.8 to 1.2 |
| N. Nonionic Polymer | 0.01 to 1 | 0.02 to 0.5 | 0.025 to 0.05 |

A=Sodium Cocoyl Isethionate (SCI) and/or Sodium Topped Cocoyl Isethionate (STCI). STCI is preferred in the present invention. It is made from topped distilled coconut fatty acid.

B=Sodium Alkyl Glyceryl Ether Sulfonate. This ingredient can be included as a lather boosting synthetic surfactant. It is made from coconut fatty alcohols. Equivalent synthetic surfactants can be used.

C=Sodium Alkyl Ether Sulfate. This is also a mild, lather boosting synthetic surfactant.

D=Sodium Cetearyl Sulfate. This is a non-soil load filler and processing aid.

E=Sodium Soap. This is a lather booster and processing aid.

F=Magnesium Soap. This is a non-soil load filler and processing aid.

G=Fatty Acid. This is a plasticizer.

H=Paraffin. This is a plasticizer.

I=Sodium Chloride. This provides bar firmness and improves bar smear.

J=Sodium sulfate. This provides bar firmness and improves bar smear.

K=Sodium Isethionate. This provides bar firmness and improves bar smear.

L=Water. This is a binder.

M=Fragrance. This is a binder and improves odor.

N=Nonionic Polymer selected from the group consisting of

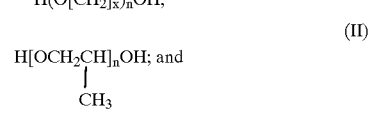

mixtures thereof;

wherein x is 2; and n has an average value of from about 2,000 to about 115,000.

Preferably the SCI/STCI bars of the present invention comprise these four ingredients: sodium cocoyl isethionate and/or sodium topped cocoyl isethionate and/or sodium alkyl glyceryl ether sulfonate, plasticizing agent, polyethylene/polypropylene glycel polymer, and binder.

The term "Plasticizer" as used herein means any material that is solid at room temperature, but is malleable at bar plodding processing temperatures of about 35° C. to about 46° C. (95° F. to 115° F.). This is the temperature of the plasticizer. At least about 20 parts by bar weight is a plasticizer excluding any synthetic surfactant which can provide some plasticizer benefits.

The term "Binder" as used herein means any material that is by itself liquid, at room temperature, and selected from water and liquid polyols. The water and liquid polyol can have a ratio of about 20:1 to about 1:5; preferably from about 5:1 to about 1:3; more preferably from about 2:1 to about 1:2. Their levels in the bar are from about 3 to about 30 parts with from about 3 to about 30 parts water and from zero to about 15 parts polyol, etc.

The formulation of synthetic detergent-based (syndet) bars is a delicate balancing act. There are numerous bar use properties to take into consideration: lather, messiness, economy, product pH bar firmness, etc.

Besides SCI/STCI the bars of the present invention can also contain other lathering surfactants, preferably, $C_{12}$–$C_{14}$ alkyl glyceryl ether sulfonate, $C_{12}$–$C_{14}$ acyl sarcosinate, methyl acyl taurates, N-acyl glutamates, alkyl sulfosuccinates, alkyl phosphate esters, ethoxylated alkyl phosphate esters, trideceth sulfates, ethoxylated alkyl sulfates and alkyl amine oxides, betaines, sultaines, and mixtures thereof, preferably as their sodium salts; and wherein at least about 10 parts by weight of said bar is said mild lathering, sodium topped, distilled, $C_{12}$–$C_{18}$ acyl isethionate (STCI).

It can also contain from 0 parts to about 40 parts, preferably from about 4 parts to about 30 preferably from 8 parts to 20 parts, of essentially saturated long chain ($C_{15-C22}$) alkyl synthetic surfactant selected from the group consisting of: alkyl sulfate, alkyl sarcosinate, alkyl glyceryl ether sulfonate, and mixtures thereof.

It can also contain from 0 parts to about 30 parts, preferably about 3 parts to about 25 parts, more preferably from about 5 parts to about 20 parts of wax, preferably paraffin, having a melting point of from about 130° F.(54° C.) to about 180° F.(82° C.).

The bar compositions of the present invention can also contain from about 0 to about 35 parts, preferably about 3 parts to about 25 parts, more preferably from about 5 parts to about 20 parts free fatty acid.

The bars can also contain from about 0 parts to about 15 parts, preferably from about 1 part to about 10 parts, more preferably from about 2 parts to about 8 parts sodium isethionate.

The bars can also contain from 0 parts to about 5 parts, preferably from about 0.1 part to about 3 parts, more preferably from about 0.2 parts to about 2 parts, sodium chloride.

The bar of this invention contains from about 3 parts to about 30 parts, preferably from about 4 parts to about 15 parts, more preferably from about 5 parts to about 10 parts by weight, water.

The bar of this invention contains from 0 parts to about 2 parts, preferably from about 0.5 parts to about 1.5 parts, more preferably from about 0.8 parts to about 1.2 parts by weight perfume.

The bars can also contain from 0 parts to about 20 parts, preferably from about 1 part to about 15 parts, more preferably from about 2 parts to about 12 parts by weight of the bar, sodium soap.

The bar of this invention contains from 0 parts to about 50 parts, preferably from about 4 parts to about 30 parts, more preferably from about 8 parts to 20 parts by weight magnesium soap.

Preferably the bars of the present invention are essentially free of greater than about 50% total soap, preferably greater than about 75% by weight, more preferably greater than about 83% by weight of the composition of total soap.

The bar of this invention contains from 0 to about 5 parts, preferably from about 0.1 part to about 3 parts; more preferably from about 0.2 parts to about 2 parts by weight, sodium sulfate.

The bars of the present invention have a pH of from about 4.0 to about 9.0, preferably about 5 to about 8, more preferably from about 6.5 to about 7.5; and wherein said bars contain by bar weight from 20 parts to about 50 parts; more preferably from about 25 parts to about 45 parts; more preferably from about 30 parts to about 40 parts of plastic material selected from the group consisting of: free fatty acid, wax, sodium and magnesium soaps, other plasticizers and mixtures thereof.

Other long chain surfactants which are equivalent to the long chain alkyl sulfate (mostly insoluble) could serve as either full or partial replacements for the long chain alkyl sulfate. Examples include long chain isethionates, sarcosinates, glyceryl ether sulfonates, etc., which have the same low solubility.

The distilled topped cocoyl isethionate of this invention differs from the acyl esters of isethionic acid salts, with high levels of $C_{16}$–$C_{18}$ acyl isethionates and no more than 25% or lower $C_{14}$ acyl groups. The present STCI bars of this invention made with only stearoyl isethionate, which has acyl chains of $C_{14}$ 3%; $C_{16}$ 50%; and $C_{18}$ 47%, tend to have poor lather properties.

Mild Synthetic Surfactants

It is noted that surfactant mildness can be measured by a skin barrier destruction test which is used to assess the irritancy potential of surfactants. In this test the milder the surfactant, the lesser the skin barrier is destroyed. Skin barrier destruction is measured by the relative amount of radio-labeled water ($^3$H—$H_2$O) which passes from the test solution through the skin epidermis into the physiological buffer contained in the diffusate chamber. This test is described by T. J. Franz in the J. Invest. Dermatol., 1975, 64, pp. 190–195; and in U.S. Pat. No. 4,673,525, Small et al., issued Jun. 16, 1987, which are both incorporated herein by reference, and which disclose a mild alkyl glyceryl ether sulfonate (AGS) surfactant based synbar comprising a "standard" alkyl glyceryl ether sulfonate mixture. (Barrier destruction testing surprisingly shows that the long chain alkyl sulfates are milder than standard AGS.) The long chain surfactants and especially long chain alkyl sulfates preferably comprise 8 to 20 parts by weight of the bars of this invention.

The sarcosinates and glyceryl ether sulfonates may be pure chain length variants or those derived from commercial oils such as coconut oil. Here, the lauryl chain length should preferably account for at least 20% to as much as 100% of the weight of the given mild surfactant.

A "high lathering surfactant" as defined herein, is one which lathers better than the long chain sodium $C_{16}$–$C_{18}$ alkyl sulfate.

A "mild surfactant" as defined herein is one that is milder than sodium dodecyl sulfate.

Numerous examples of other surfactants in general are disclosed in the patents incorporated herein by reference. They include limited amounts of anionic acyl sarcosinates, methyl acyl taurates, N-acyl glutamates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these other surfactants are $C_8$–$C_{22}$, preferably $C_{10}$–$C_{18}$. Alkyl glycosides and methyl glucoside esters are preferred mild nonionics which may be mixed with other mild anionic or amphoteric surfactants in the compositions of this invention.

The bars of this invention can have from 0 to about 10 parts of high lathering, non-mild surfactants and still maintain the preferred mildness requirement of the bar. Examples of these surfactants include linear alkyl benzene sulfonates and shorter chain or traditional (coconut) alkyl sulfates.

A preferred syndet bar can contain a mixture of sodium topped distilled $C_{12}$–$C_{18}$ cocoyl isethionate (STCI) and sodium linear alkylbenzene sulfonate in a ratio of from about 35:1 to about 15:1, preferably from about 30:1 to about 20:1.

Plasticizers

The preferred plasticizers of the present invention are: (1) fatty acid (2) sodium soap, (3) wax, preferably paraffin wax, and (4) mixtures thereof.

The fatty acid material which is desirably incorporated into the present invention includes material ranging in hydrocarbon chain length of from about 10 to about 22, essentially saturated. These fatty acids can be highly purified individual chain lengths and/or crude mixtures such as those derived from fats and oils. The industry term "triple pressed stearic acid" comprises about 45% stearic and 55% palmitic acids. Thus, this is its meaning as used herein.

The composition may include soaps derived from hydrocarbon chain lengths of from about 10 to about 22 (including carboxyl carbon) and are preferably saturated. It is preferred that the soap be the sodium salt, but other soluble soap can be used. Potassium, ammonium, triethanolammonium, and mixtures thereof, are deemed acceptable. The soaps are preferably prepared by in situ saponification or ion exchange with a halide salt of the corresponding fatty acids, but they may also be introduced as preformed soaps.

"Insoluble" soaps, e.g., magnesium and zinc soaps, are not included in the level of "sodium soap" in the composition definition. However, insoluble soaps can be used as non-lathering, non-soil-load diluents and processing aids.

The waxes are selected from the group consisting of beeswax, spermaceti, carnauba, baysberry, candelilla, montan, ozokerite, ceresin, paraffin, synthetic waxes such as Fisher-Tropsch waxes, microcrystalline wax, and mixtures thereof.

A highly preferred component of this invention is a wax, preferably paraffin wax having a melting point (M.P.) of from about 130° F. to about 180° F. (54°–82° C.), preferably from about 140° F. to about 165° F. (60°–74° C.), and most preferably from about 142° F. to about 160° F. (61°–71° C.). "High melt" paraffin is paraffin that has a melting point of about 150°–160° F. (66°–71° C.). "Low melt" paraffin is paraffin that has a melting point of about 130°–140° F. (54°–60°). A preferred paraffin wax is a fully refined petroleum wax which is odorless and tasteless and meets FDA requirements for use as coatings for food and food packages. Such paraffins are readily available commercially. A very suitable paraffin can be obtained, for example, from The National Wax Co. under the trade name 6975.

The wax, preferably paraffin, is preferably present in the bar in an amount ranging from about 3 parts to about 30 parts by weight. The wax ingredient is used in the product to impart skin mildness, plasticity, firmness, and processability. It also provides a glossy look and smooth feel to the bar.

The Binder

This invention contains water and can contain a liquid water-soluble aliphatic polyol. The polyol may be saturated or contain ethylenic linkages; it must have at least two alcohol groups attached to separate carbon atoms in the chain, and must be water soluble and liquid at room temperature. If desired, the compound may have an alcohol group attached to each carbon atom in the chain. Among the compounds which are effective are ethylene glycol, propylene glycol and glycerine. A preferred polyol is dipropylene glycol, which is effective in amounts as low as about 0.1 and about 0.25 parts by weight, preferably the level is from about 0.5 parts to about 5 parts; and more preferably from about 0.5 parts to about 2 parts by weight of the bar.

Nonionic Polyethylene/Polypropylene Glycol Polymers

The bar compositions of the present invention comprise from about 0.01 parts to about 1 parts, preferably from about 0.02 parts to about 0.5 parts by bar weight, and more preferably from about 0.025 parts to about 0.05 parts of a polymer of ethylene oxide and/or propylene oxide.

The polymers of the present invention are characterized by the general formulas:

$$H(O[CH_2]_x)_nOH; \quad (I)$$

$$H[OCH_2CH]_nOH; \text{ and} \quad (II)$$
$$\quad | \quad$$
$$\quad CH_3$$

mixtures thereof; (III)

wherein x is 2; and n has an average value of from about 2,000 to about 115,000, preferably from about 5,000 to about 100,000, more preferably from about 23,000 to about 90,000.

Polymers useful herein that are especially preferred are PEG-2M wherein x equals 2 and n has an average value of about 2,000 (PEG 2-M is also known as Polyox WSR® N-10 from Union Carbide and as PEG-2,000); PEG-5M wherein x equals 2 and n has an average value of about 5,000 (PEG 5-M is also known as Polyox WSR® 35 and Polyox WSR® N-80, both from Union Carbide and as PEG-5,000 and Polyethylene Glycol 200,000); PEG-7M wherein x equals 2 and n has an average value of about 7,000 (PEG 7-M is also known as Polyox WSR® ( N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR-205 and Polyox WSR® N-3000 both from Union Carbide); and PEG-90M wherein x equals 2 and n has an average value of about 90,000 (PEG-90M is also known as Polyox WSR®-301 from Union Carbide.)

All percentages describing the polymer in this section of the description herein, are molar, unless otherwise specified.

Other Optional Ingredients

Other ingredients of the present invention are selected for the various applications. For example, perfumes can be used in formulating the skin cleansing products, generally at a level of from about 0.1 parts to about 1.5 parts by weight of the composition. Vegetable oils, such as peanut and soybean oil can be added at levels up to about 10 parts, preferably from about 2 to about 6 parts. Alcohols, hydrotropes, colorants, and fillers such as talc, clay, calcium carbonate, oils and dextrin can also be used at appropriate levels. Preservatives, e.g., trisodium etidronate and sodium ethylenediaminetetraacetate (EDTA), generally at a level of less than about 1 part of the composition, can be incorporated in the cleansing products to prevent color and odor degradation. Antibacterials can also be incorporated, usually at levels up to about 1.5 parts. Salts, both organic and inorganic, can be incorporated. Examples include sodium chloride, sodium isethionate, sodium sulfate, and their equivalents.

Optional Adjunct Odor-Reducing or Odor-Controlling Materials

The compositions of the present invention can also contain an effective, i.e., odor-controlling, amount of various additional zeolite and non-zeolite odor-controlling materials to further expand their capacity for controlling odors, as well as the range of odor types being controlled. Such materials include, for example, cetyl pyridinium chloride, zinc chloride, EDTA, etidronate, BHT, and the like.

A preferred zeolite is substantially free of particles sized greater than 30 microns, and in fact is substantially free of particles sized over 15 microns for acceptable bar feel. "Substantially free" means that the larger particles are less than about 5 parts, preferably less than about 4 parts, more preferably less than about 3 parts, as measured by laser light scattering.

The following patents disclose or refer to ingredients and formulations which may be useful in the STCI bars of this invention, and are incorporated herein by reference:

| U.S. Pat. No. | Issue Date | Inventor(s) |
| --- | --- | --- |
| 4,234,464 | 11/1980 | Morshauser |
| 4,061,602 | 12/1977 | Oberstar et al. |
| 4,472,297 | 9/1984 | Bolich et al. |
| 4,491,539 | 1/1985 | Hoskins et al. |
| 4,540,507 | 9/1985 | Grollier |
| 4,704,224 | 11/1987 | Saud |
| 4,812,253 | 3/1989 | Small et al. |
| 4,820,447 | 4/1989 | Medcalf et al. |
| 4,954,282 | 9/1990 | Rys et al. |
| 5,154,849 | 10/1992 | Visscher, et al. |

The bars of the present invention have a pH of from about 4 to about 9 in a 1 part aqueous solution. The preferred pH is from about 5 to about 8, more preferably about 6.5 to about 7.5.

A Method of Making SCI/STCI Bars

Crutching (A, B and C are Alternative Procedures)

A. 1. If used, add melted cetearyl sulfate, and/or AGS and/or AE$_3$S (50°–75° C.); begin agitation.
  2. If used, add NaCl, then TiO$_2$, then EDTA, then etidronate, and then zeolite, and bring crutcher mixture to 85° C. under low agitation.
  3. Add premeasured caustic and Mg(OH)$_2$, if used, and continue to mix slowly.
  4. Steam sparge to 85° C. before adding remaining ingredients.
  5. Add fatty acid and mix for 5–10 minutes at 85° C.
  6. Add the paraffin, SCI, STCI, SI (sodium isethionate) and continue mixing slowly for approximately 15–30 minutes while maintaining the mix temperature at 85° C.
  7. If used, add glycerin slowly under constant agitation.

B. 1. Add paraffin, SCI, STCI, SI and begin agitating slowly while maintaining the temperature at 85° C.
  2. If used, add molten cetearyl sulfate, and/or AGS, and/or AE3S (50°–75° C.) and maintain slow agitation and recirculation.
  3. If used, add NaCl, then TiO$_2$ then EDTA, then etidronate, and then zeolite, increasing the temperature in the 85° C. range under low agitation and steam sparging.
  4. Add the premeasured caustic and Mg(OH)$_2$, if used, and continue to mix slowly.
  5. Add the required fatty acid and mix for another 10 minutes at 85° C. Check for uniform consistency of the crutcher batch.
  6. If used, add glycerin slowly under constant agitation.

C. 1. If used, add molten cetearyl sulfate, AGS and/or AE$_3$S (50°–75° C.) to the crutcher and begin slow agitation.
  2. Add the paraffin sodium topped, distilled cocoyl isethionate (STCI), sodium cocoyl isethionate (SCI), sodium isethionate (SI) and continue to mix with agitation and begin recirculation.
  3. If used, add NaCl, then TiO$_2$, then EDTA, then etidronate, and then zeolite, increasing the temperature to 85° C. while agitating and recirculating and steam sparging.
  4. Add the premeasured caustic and Mg(OH)$_2$, if used, and continue to mix slowly.
  5. Add the required fatty acid and mix for another 10 minutes at 85° C. Check for uniform consistency of the crutcher batch and continue to mix until fluid and lump free.
  6. If used, add glycerin slowly under constant agitation.

Drying

The crutcher mix is dried and cooled using a combination flash chamber and chill roll or chill belt. The crutcher mix is first heated to approximately 265°–275° F. (130°–135° C.) by a heat exchanger and then flash dried in a chamber above the chill roll or chill belt. The chill belt or chill roll provides a uniform, thin cool (85°–95° F.; 29°–35° C.) product in flake or chip form. Typical moisture for the flake is from about 3 parts to about 15 parts, preferably from about 5 parts to about 10 parts. The way to regulate the moisture, in the order of preference, are: (1) increasing or decreasing steam pressure on the heat exchanger; (2) increasing or decreasing crutcher mix rate to the heat exchanger, and (3) increasing or decreasing crutcher mix temperature to the heat exchanger.

Amalgamating

The flakes are weighed and added to a batch amalgamator to obtain uniform flake size and a course mixture of additives that may be brought into the flake mixture (syndet or soap).

(Alternative Procedures):

A. Preweighed flakes may be amalgamated to uniform size and premeasured amounts of the nonionic polyethylene/polypropylene glycol polymer and optional dipropylene glycol, glycerin, and the zeolite deodorizing powder are added into the base flakes and mixed for several minutes with no perfume being added.

B. Preweighed flakes may be amalgamated to uniform size and a premeasured amount of the nonionic polyethylenelpolypropylene glycol polymer and optional dipropylene glycol, glycerin, etc. is added into the base flakes and admixed for several minutes before; then adding a premeasured amount of perfume. Continue amalgamating for at least one minute to thoroughly mix together the ingredients.

(Note: The nonionic polyethylene/polypropylene glycol polymer is either added as a dry powder or is prehydrated with a minimum amount of water to form a gel consistency, preferably a completely clear gel).

Milling

The 3-roll soap mills are set up with the first roll at ~120° F. (49° C.), the second roll at ~100° F. (38° C.), and the final roll at ~68° F. (20° C.). The material is passed through the mills several times to provide a homogeneous mixture of perfume and dried flakes. Typically the milled material has a temperature of 44° to 54° C.

Plodding and Stamping

The plodder is set up with the barrel temperature at about 115° F. (46° C.) and the nose temperature at 114°–122° F. (45°–50° C.). The ideal plodder is a dual stage plodder that allows use of a vacuum of about 15–25 inches (38–64 cm) of Hg. The plugs should be cut in 5 inch (13 cm) sections and stamped with a cold die block using die liquor such as alcohol, if appropriate.

Examples and Formulas

The following examples and formulas are illustrative and are not intended to limit the scope of the invention. The methods of making milled bars are well known. All levels and ranges, temperatures, results, etc. used herein are approximations unless otherwise specified. Therefore, the percentages do not necessarily add up to 100 parts. All component levels are percentages based on weight.

High Melt Point Paraffin melts at about 158° F. (70° C.). Low Melt Point Paraffin melts at about 131° F. (55° C.).

TABLE 1A

| Component | Ex. 1 | Ex. 2 | Ex. 3 | Ex. 4 |
|---|---|---|---|---|
| Na-Cocoyl Isethionate | 19.58 | | | |
| Na-Topped Cocoyl Isethionate (STCI) | | 19.58 | 27.18 | 18.85 |
| Sodium Alkyl Glyceryl Ether Sulfonate | 19.58 | 19.58 | 14.58 | 18.85 |
| Polyethylene glycol polymer[1] | 0.025 | 0.025 | 0.025 | 0.05 |
| Sodium Soap | 9.7 | 9.7 | 3.36 | 6.50 |
| Magnesium Soap | 3.73 | 3.73 | 6.66 | 11.00 |
| Free Fatty Acid (STCI) | 0.13 | 0.13 | 2.03 | 0.35 |
| Paraffin - High Melt Point | 27.42 | 27.42 | 16.37 | 23.00 |
| NaCl | 0.67 | 0.67 | 0.5 | 0.64 |
| Na2SO4 | 1.12 | 1.12 | 1.02 | 1.08 |
| Na-Isethionate | 1.12 | 1.12 | 2.48 | 1.75 |
| Glycerin | 3.70 | 3.70 | 8.39 | 4.00 |
| Water | 6 | 6 | 7 | 6 |
| Fragrance | 1 | 1 | 1 | 1 |
| Palmitic Acid | | 0.15 | | 0.64 |
| Myristic Acid | | 0.15 | | 0.61 |
| Lauric Acid | | | 0.28 | 0.08 |
| Stearic Acid | | | 3.31 | |
| TiO$_2$ | 0.35 | 0.35 | 0.25 | 0.35 |
| Trisodium EDTA | 0.1 | 0.1 | 0.1 | 0.1 |
| Trisodium Etidronate | 0.1 | 0.1 | 0.1 | 0.1 |
| Minors[2] | Balance | Balance | Balance | Balance |
| Total Parts = 100 | | | | |

[1] Polyox WSR-301 ®, 90-M, available from Union Carbide Co.
[2] Minors includes unreacted feedstocks and products of secondary side reactions. See Table 1B for the chainlengths of the acyl isethionates.

TABLE 1B

| Chainlengths of Acyl Isethionates: | Ex. 1 | Ex. 2 | Ex. 3 | Ex. 4 |
|---|---|---|---|---|
| C$_8$ | 8 | 0 | 0 | 0 |
| C$_{10}$ | 7 | 0 | 0 | 0 |
| C$_{12}$ | 53 | 60 | 60 | 60 |
| C$_{14}$ | 17 | 23 | 23 | 23 |
| C$_{16}$ | 7 | 10 | 10 | 10 |
| C$_{18}$ | 4 | 7 | 7 | 7 |
| C$_{18:1}$ | 3 | 1 | 1 | 1 |
| Total Isethionate | 100 | 100 | 100 | 100 |

Examples 1–4 above are made by the methods described hereinbefore in the Section entitled "A Method of Making SCI/STCI Bars".

What is claimed is:

1. A personal cleansing bar composition consisting essentially of:
   A. from about 10 parts to about 70 parts by bar weight of a mild synthetic surfactant consisting essentially of:
      i.) a mild synthetic surfactant selected from the group consisting or sodium cocoyl isethionate, sodium topped cocoyl isethionate and mixtures thereof; and
      ii) a mild synthetic surfactant selected from the group consisting of essentially saturated C$_{15}$–C$_{22}$ alkyl sulfate, essentially saturated C$_{15}$–C$_{22}$ alkyl sarcosinate, essentially saturated C$_{15}$–C$_{22}$ alkyl glyceryl ether sulfonate, and mixtures thereof;
   B. from about 0.01 to about 0.05 parts by bar weight of a nonionic polymer;
   C. from about 0 parts to about 50 parts by bar weight of a wax having a melting point of from about 130° F.(54° C.) to about 180° F.(82° C.);
   D. from about 0 parts to about 60 parts by bar weight lathering mild synthetic surfactant selected from the group consisting of methyl acyl taurates, N-acyl glutamates, alkyl sulfosuccinates, alkyl phosphate esters, ethoxylated alkyl phosphate esters, trideceth sulfates, ethoxylated alkyl sulfates and alkyl amine oxides, betaines, sultaines, C$_{12}$–C$_{14}$ alkyl glyceryl ether sulfonate, C$_{12}$–C$_{18}$ acyl sarcosinate, and mixtures thereof;
   E. from about 0 parts to about 35 parts by bar weight fatty acid;
   F. from about 0 parts to about 20 parts by bar weight sodium soap;
   G. from about 8 parts to about 20 parts by bar weight Mg soap;
   H. from 0 parts to about 5 parts by bar weight sodium chloride;
   I. from about 3 parts to about 30 parts by bar weight water; and
wherein the nonionic polymer is selected from the group consisting of:

(I)

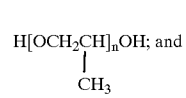
(II)

(III)

mixtures thereof;

wherein x is 2; and n has an average value or from about 2,000 to about 115,000 and wherein the composition is essentially free of greater than about 20% by weight of the composition of milled wheat flour; and wherein the pH is from about 4 to about 9 and wherein the personal cleansing bar compositions contain no more than about 25% by weight of total soap.

2. The composition of claim 1 wherein the level of nonionic polymer is from about 0.025 parts to about 0.05 parts by bar weight.

3. The composition of claim 2 wherein n has an average value of from about 5,000 to about 100,000.

4. The composition of claim 3 wherein n has an average value of from about 23,000 to about 90,000.

5. The composition of claim 1 comprising from about 12 to about 60 parts by bar weight of a mild synthetic surfactant selected from the group consisting of sodium cocyl isethionate, sodium topped cocyl isethionate and mixtures thereof, and from about 5 parts to about 30 parts by bar weight of essentially saturated C15–C22 alkyl glyceryl ether sulfonate.

6. A personal cleansing bar composition consisting essentially of:
   A. from about 10 parts to about 70 parts by bar weight of a mild synthetic surfactant consisting essentially of:
      i.) from about 12 parts to about 60 parts by bar weight of a mild synthetic surfactant selected from the group consisting of sodium cocoyl isethionate, sodium topped cocoyl isethionate, and mixtures thereof; and ii.) from about 5 parts to about 30 parts by bar weight of essentially saturated $C_{15}$–$C_{22}$ alkyl glyceryl ether sulfonate;

B. from about 0.01 to about 0.05 parts by bar weight of a nonionic polymer;

C. from about 3 parts to about 45 parts by bar weight of a wax having a melting point of from about 130° F. (54° C.) to about 180° F. (82° C.);

D. from about 0 parts to about 60 parts by bar weight lathering mild synthetic surfactant selected from the group consisting of methyl acyl taurates, N-acyl glutamates, alkyl sulfosuccinates, alkyl phosphate esters, ethoxylated alkyl phosphate esters, trideceth sulfates, ethoxylated alkyl sulfates and alkyl amine oxides, betaines, sultaines, $C_{12}$–$C_{14}$ alkyl glyceryl ether sulfonate, $C_{12}$–$C_{18}$ acyl sarcosinate, and mixtures thereof;

E. from about 0 parts to about 35 parts by bar weight fatty acid;

F. from about 0 parts to about 20 parts by bar weight sodium soap;

G. from about 8 parts to about 20 parts by bar weight Mg soap;

H. from 0 parts to about 5 parts by bar weight sodium chloride;

I. from about 3 parts to about 30 parts by bar weight water; and wherein the nonionic polymer is selected from the group consisting of:

$$H(O[CH_2]_x)_nOH; \quad (I)$$

$$H[OCH_2CH]_nOH; \text{ and} \quad (II)$$
$$\phantom{H[OCH_2CH]_n}|$$
$$\phantom{H[OCH_2CH]_n}CH_3$$

mixtures thereof; (III)

wherein x is 2; and n has an average value of from about 2,000 to about 115,000 and wherein the composition is essentially free of greater than about 20% by weight of the composition of milled wheat flour; and wherein the pH is from about 4 to about 9 and wherein the personal cleansing bar compositions contain no more than about 25% by weight of total soap.

7. The composition of claim 6 wherein the level of nonionic polymer is from about 0.025 parts to about 0.05 parts by bar weight.

8. The composition of claim 6 wherein the bar comprises from about 15 parts to about 50 parts by bar weight of sodium topped cocoyl isethionate and from about 10 parts to about 20 parts of essentially saturated $C_{15}$–$C_{22}$ alkyl glyceryl ether sulfonate.

9. The composition of claim 8 wherein the wax is selected from the group consisting of beeswax, spermaceti, carnauba, baysberry, candelilla, montan, ozokerite, ceresin, paraffin, synthetic waxes such as Fisher-Tropsch waxes, microcrystalline wax, and mixtures thereof.

10. The composition of claim 9 wherein the wax is parraffin wax having a melting point of from about 140° F. (60° C.) to about 165° F. (74° C.).

\* \* \* \* \*